United States Patent [19]

Jones

[11] Patent Number: 4,643,019
[45] Date of Patent: * Feb. 17, 1987

[54] POROUS END PLUG DISK FOR TESTING CORE SAMPLES

[75] Inventor: Stanley C. Jones, Littleton, Colo.

[73] Assignee: Marathon Oil Company, Findlay, Ohio

[ * ] Notice: The portion of the term of this patent subsequent to Dec. 31, 2002 has been disclaimed.

[21] Appl. No.: 791,627

[22] Filed: Oct. 25, 1985

Related U.S. Application Data

[63] Continuation-in-part of Ser. No. 651,561, Sep. 14, 1984, Pat. No. 4,561,289.

[51] Int. Cl.⁴ .............................................. G01N 15/08
[52] U.S. Cl. .................................................... 73/38
[58] Field of Search ............................................ 73/38

[56] References Cited

U.S. PATENT DOCUMENTS 4,433,571 2/1984 Snow, Jr. .............................. 73/37.5
4,561,289 12/1985 Jones ........................................ 73/38

Primary Examiner—Stewart J. Levy
Assistant Examiner—Joseph W. Roskos
Attorney, Agent, or Firm—Jack L. Hummel; Rodney F. Brown

[57] ABSTRACT

Improved end plugs for abutting core samples during porosity and permeability testing. The end plug has a face having at least one circular channel and a plurality of radial channels formed on its surface which are in fluid communication with the circular channel. The face abuts a porous disk which in turn abuts the core sample.

8 Claims, 4 Drawing Figures

POROUS END PLUG DISK FOR TESTING CORE SAMPLES

RELATED APPLICATION

This application is a continuation-in-part application of parent application titled, "Improved Perforated End Plug Plate For Testing Core Sample," Ser. No. 651,561, filed on Sept. 14, 1984 now U.S. Pat. No. 4,561,289.

FIELD OF THE INVENTION

The present invention relates to an end plug design which is placed at opposing ends of core samples obtained from an underlying rock formation when conducting tests on the cores such as ascertaining permeability and porosity of the cores.

BACKGROUND OF THE ART

Two important parameters for evaluating production of an underlying oil or gas bearing formation are to determine the permeability and porosity of core samples taken from the formation. A measurement of permeability of the core provides an indication as to how fast the oil or gas will flow from the formation upon production whereas a measurement porosity provides information as to the amount of oil or gas contained within the formation. In conducting such tests on core samples, especially when overburden pressures are applied to the core samples, perforated end plug plates are used on each end of the sample to aid in the distribution of gas into the sample.

The determination of both porosity and permeability are based upon complex mathematical determinations and both are common measurements in the oil and gas industry. An understanding of these mathematical formulas is not necessary for the understanding of the present invention. However, a discussion of the mathematical formulas for determining Klinkenberg permeability, the Klinkenberg slip factor and the Forcheimer turbulence factor observed in core plugs is set forth in the inventor's prior publication entitled "A Rapid Accurate Unsteady-State Klinkenberg Permeameter", *Society of Petroleum Engineers Journal,* October 1972, pages 383-397. In that publication, a method and apparatus for performing permeability tests on core samples is set forth. In that disclosure, each sample core is manually loaded into a Hassler core holder and the sleeve contained therein is then pressurized to simulate an overburden pressure. A gas, such as nitrogen, is then introduced through an end plate having circular formed holes into one end of the core and the passage of the gas through the core into a second end plate is then determined to ascertain the permeability. End plug plates are utilized at opposing ends of the core sample to aid in the distribution of gas and to provide structural support to the core sample.

In addition, prior to the filing of this invention, a patentability search was conducted on the above identified related application which uncovered the following patents:

| Inventor | Reg. No. | Reg. Date |
|---|---|---|
| Bowman | 966,078 | Aug. 2, 1910 |
| Dietert et al. | 2,516,188 | July 25, 1950 |
| Reichertz | 2,539,355 | Jan. 23, 1951 |
| Leas | 2,618,151 | Nov. 18, 1952 |
| Herzog et al. | 2,737,804 | Mar. 13, 1956 |

-continued

| Inventor | Reg. No. | Reg. Date |
|---|---|---|
| Dotson | 2,745,057 | May 8, 1956 |
| Donaldson | 3,158,020 | Nov. 24, 1964 |
| Heuer, Jr. et al. | 3,199,341 | Aug. 10, 1965 |
| McMillen | 3,839,899 | Oct. 8, 1974 |
| Wilkins | 4,043,407 | Aug. 23, 1977 |
| Turner et al. | 4,083,228 | Apr. 11, 1978 |
| Neri | 4,227,397 | Oct. 14, 1980 |
| Wiley | 4,253,327 | Mar. 3, 1981 |
| Heitmann et al. | 4,287,754 | Sept. 8, 1981 |
| Pezzi | 4,403,501 | Sept. 13, 1983 |
| Hains | 4,430,890 | Feb. 14, 1984 |
| Holt | 4,454,095 | June 12, 1984 |

Only the following disussed patents disclosed types of perforated end plugs.

The Wiley patent sets forth a method and apparatus for measuring core permeability at overburden conditions of both pressure and temperature. Each core must be manually loaded into a sleeve having end plugs inserted into the sleeve. Then the entire assembly is placed into a hydrostatic cell wherein hydraulic fluid is pressurized around the end plugs and the sleeve to simulate the overburden pressure. The fluid is then injected through one end plug, through a sintered plate, through the core, out a second sintered plate and through the opposing end plug.

In Leas, a manually loaded cell for measuring relative permeability is disclosed wherein a flexible elastic sleeve selectively pressurizes the sides of the core during testing so as to simulate overburden stress. Fluids are injected into the end of the core to measure the permeability of the core. To insert or remove the core, a vacuum is pulled around the elastic sleeve so that the core can be manually removed or inserted. Porous disks are placed on each end of the core to aid in the distribution of the fluid to and from the core. The porous disks of Leas have two embodiments. The first embodiment has a rectangular grid of channels on the side of the plate abutting the core sample and the second embodiment provides a shallow cylindrical cavity. The cavity and grooves both are in fluid communication with a center hole. The opposite side of each plate is flat.

Heuer, Jr. et al. discloses a method and apparatus for measuring compressibility of core samples by encapsulating the core sample in a fluid-impervious sheet such as flexible plastic and then suspending the core sample in a pressure vessel and subjecting the sample to high pressure while passing fluids to and from opposing ends of the core sample through fluid-permeable steel disks.

The Morgan patent sets forth a method of sealing cores while determining the permeability of the core by providing a counter-pressure environment around the core with an atmosphere of non-wetting fluid. The pressure eliminates the use of sealing material such as pitch, tar, or a separate sealing medium such as plastic or rubber. A capillary diaphragm is used on opposing ends of the core sample.

A disadvantage with prior art approaches as found in the Leas "waffle" design occurs when the applied stresses cause the plate to deform (imprint) the ends of the core. This not only may damage the core, but also blocks the gas passageways in the plate possibly effectuating a less than uniform distribution of gas in the core. Non-uniform distribution of gas may cause errors to occur in the permeability or porosity readings.

None of the above discussed patents set forth an end plug design of the present invention which includes the plug, having an array of fluid passage channels formed thereon, and a two-sided porous disk, one side abutting the fluid passage channels and the other side abutting the core.

SUMMARY OF THE INVENTION

The end plug design of the present invention enables one to maximize uniform fluid flow distribution into a core sample while minimizing damage to the physical ends of the core sample when conducting tests such as permeability and porosity on the core sample subject to overburden stresses. The end plug has a face with a porous disk placed thereon. An array of radial and circular channels is formed in the face of the end plug which abuts one flat surface of the disk and enables the delivery of a fluid into the end of a core sample which abuts the opposite flat surface of the disk.

DETAILED DESCRIPTION

Figure 1:
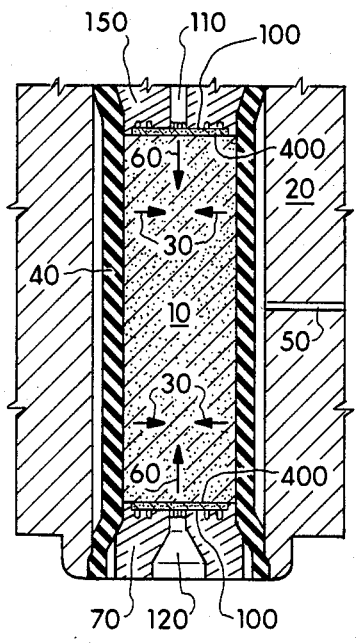
FIG. 1 is a cross-sectional view of the end plug and disk of the present invention engaging the upper and lower ends of a core sample under stress in a test chamber.

FIG. 1 shows a core sample 10 being held in a test chamber 20 having two end plugs 70 and 150. An elastic sleeve 40 applies radial forces 30 to core sample 10 by means of pressurized fluid flowing through passageway 50. In addition, piston 70 which serves as one end plug and retainer 150 which serves as the other end plug apply an axial stress 60 to the ends of the core sample 10.

The present invention relates to the design of the end plugs 70 and 150. Each end plug has a channeled face 100 with a porous disk 400 mounted thereon. The end plugs are on opposing ends of the core sample 10 and function to distribute a fluid, such as a gas, into the core sample 10 or collect a fluid from the core sample 10. Passageway 110 delivers fluid to the end plug 150 and passageway 120 expels fluid from end plug 70 in the course of a permeability test.

Figure 2:
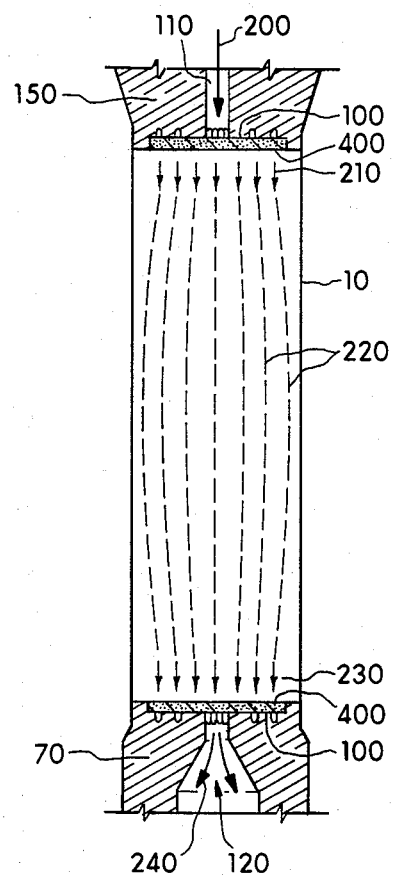
FIG. 2 is an illustration showing the uniform distribution of gas being extended through the disks to and from the core sample.

The present invention can be used in a number of types of tests, such as electrical resistivity, with a number of fluids. A permeability test is shown in FIG. 2, by way of example, which uses a helium gas. The helium gas 200 is delivered through upper passageway 110 to the face 100 of upper end plug 150 and through the disk 400 into the upper end of the core 10. As can be witnessed, the function of the face 100 and disk 400 is to distribute uniformly, as shown by arrows 210, the incoming helium gas 200 over the top surface of the core sample 10. The gas is evenly distributed throughout the same core 10 as represented by dotted lines 220 and is uniformly collected as represented by arrows 230 by the disk 400 and face 100 of end plug 70 for delivery out from the core sample 10 as shown by arrows 240. The distribution of gas is uniform despite the application of the axial overburden stress to the core sample 10.

Figure 3:
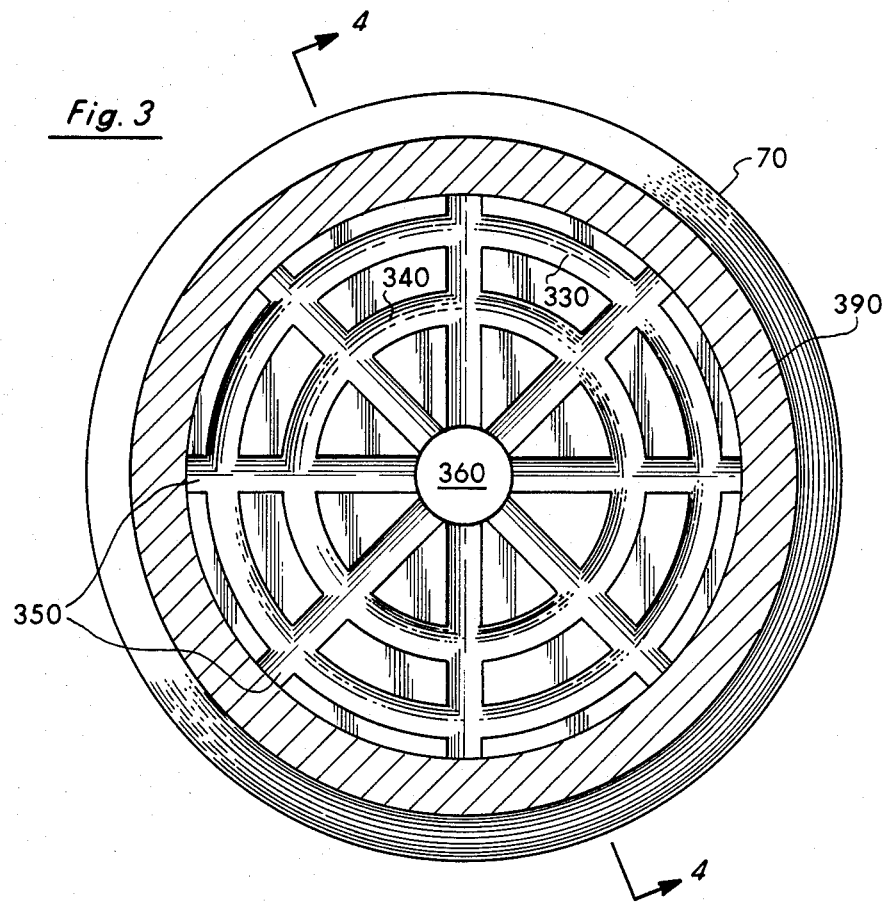
FIG. 3 is a top planar view of the lower channeled face of the end plug.
Figure 4:
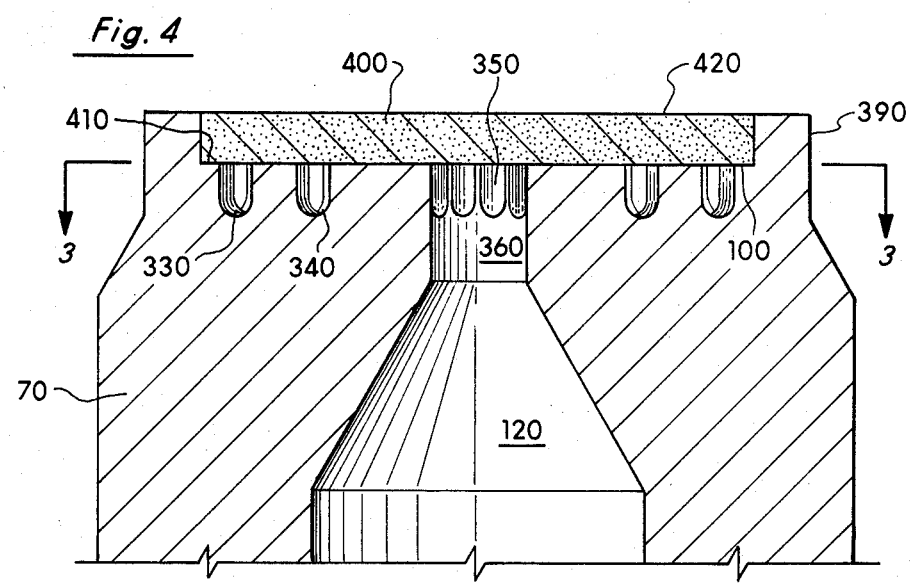
FIG. 4 is a cut-away view of the lower plug and disk along lines 4—4.

The details of the channeled face 100 and disk 400 of the present invention as shown in FIGS. 3 and 4 as aligned in plug 70 with the lower end of core. Plug 70 is cylindrically shaped and has a cavity which forms the face 100 and accepts the disk 400. The diameters of the disk and face are preferably the same and are to be used with cores of, for example, one-inch diameter. In the preferred embodiment, the face 100 has a first circular channel 330, a second circular channel 340, a plurality of outwardly directed radial channels 350, and a central channel 360, from which radial channels 350 are directed, formed therein. The central channel 360 establishes fluid communication between passageways 110 and 120 and channels 350, 330 and 340.

Face 100 as shown in FIG. 4, abuts downward surface 410 of porous disk 400 and exposes the circular (330 and 340) and radial (350) array of channels interconnected with central channel 360 shown in FIG. 3 to surface 410 of disk 400. Upward surface 420 of lower disk 400 abuts the end of core sample 10. Upper plug 150 has a similar configuration and face 100 and disk 400 are arranged correspondingly.

The channeled face 100 in the preferred embodiment is made from No. 17-4PH stainless steel for non-corrosive gas service or from Hastelloy-C for corrosive liquid serivce. The disk 400 is preferably made from a porous metal, e.g., a 316 stainless steel for non-corrosive gas service or a significantly less corrosive stainless steel, e.g., Hastelloy-C 276 for corrosive liquid service. The pore size of the disk can range from 100 microns to 0.5 microns. Relatively large pore sizes are used where little filtration is required and relatively smaller pore sizes are used where greater filtration is required. Porous disks meeting these requirements can be obtained from Mott Metallurgical Corp., Farmington CN, U.S.A.

Disk 400 is pressed into the corresponding cavity in the end plug 150 or 70 as shown in FIG. 4 to abut face 100. The end plug 70 or 150 has a lip 390 around the cavity to fittingly retain disk 400. While the channels as shown having a semi-circular cross-section, it is to be expressely understood that a rectangular cross-section or other design could also be used.

This specific arrangement of porous disk and channels aids in the uniform distribution of gas into the core sample and uniform collection of gas out of the core sample. The arrangement also provides mechanical support at the high overburden stresses applied to the core sample when porosity and permeability tests are cnducted so that the ends of the core samples ar not damaged. In particular, the present invention minimizes damage to the core ends by providing a substantially flat porous surface. The flat surface minimizes deformation of the core ends while the pores permit the uniform distribution of gas over the entire end of the plug. If the ends of the core samples are damaged, an error in the test, such as permeability and porosity, could result.

It is to be expressly understood that under the teachings of the present invention, while two channels 330 and 340 are shown in the preferred embodiment, at least one circular channel is required to provide fluid interconnection between the radial channels 350. Likewise, while eight radial channels are shown in the preferred embodiment, this also could be more or less.

In one embodiment, the face of the end plug is approximately 0.875 inch in diameter. Each channel is 0.06 inch wide and 0.045 inch deep. The disk is approximately 0.875 inch in diameter and 0.062 inch thick. The total diameter of the top surface of the end plug including the disk and lip is approximately one inch.

In the preferred embodiment, the face of the end plug is a continuous surface of the plug. The channels are machined directly into the plug. However, other alternatives for the face of the end plug are possible. For example, the face of the end plug may be a removable plate having the channels formed therein rather than directly on the end plug. The channeled plate is pressed into the end plug cavity ahead of the disk and provides fluid communication between the flui passageway in the plug and the disk in the same manner as if the channels are contained directly in the plug.

While a preferred embodiment of the present invention has been disclosed it is to be expressly understood that changes and modifications could be made thereto without departing from the scope of the invention as set forth in the following claims.

I claim:

1. An end plug abutting an end of a core sample during testing of said core sample, said end plug being in fluid communication with a fluid and capable of delivering said fluid into said end of said core sample, said end plug comprising:
   a porous disk (400) having a substantially flat first surface (410) abutting a face (100) of said end plug and a substantially flat second surface (420) abutting said end of said core sample;
   said face (100) having at least one circular channel (330, 340) formed therein between the center and outer circumference of said face, a plurality of radial channels (350) formed in said face in fluid communication with said at least one circular channel (330, 340) and a central channel (360) formed in the center of said face from which said plurality of radial channels (350) emanate outwardly to said circumference;
   said central channel (360) in fluid communication with said fluid for extending said fluid through said radial channels (350) into said at least one circular channel (330, 340), through said porous disk and into said core sample.

2. The end plug of claim 1 wherein said formed circular and radial channels (330, 340, 350) have a semi-circular cross-section.

3. The end plug of claim 1 wherein said face and porous disk are circular and have substantially the same diameter.

4. The end plug of claim 1 wherein said face is a continuous surface of said end plug.

5. An end plug abutting an end of a core sample during testing of said core sample, said end plug being in fluid communication with a fluid and capable of delivering said fluid into said end of said core sample, said end plug comprising:
   a porous disk (400) having a substantially flat first surface (410) abutting a face (100) of said end plug and a substantially flat second surface (420) abutting said end of said core sample;
   said face (100) having two circular channels (330, 340) formed therein between the center and outer circumference of said face, a plurality of radial channels (350) formed in said face in fluid communication with said two circular channels (330, 340) and a central channel (360) formed in the center of said face from which said plurality of radial channels (350) emanate outwardly to said circumference;
   said central channel (360) in fluid communication with said fluid for extending said fluid through said radial channels (350) into said two circular channels (330, 340), through said porous disk and into said core sample.

6. The end plug of clam 5 wherein said formed circular and radial channels (330, 340, 350) have a semi-circular cross-section.

7. The end plug of claim 5 wherein said face and porous disk are circular and have substantially the same diameter.

8. The end plug of claim 5 wherein said face is a continuous surface of said end plug.

* * * * *